United States Patent
Adriansens (10) Patent No.: US 9,409,661 B2
(45) Date of Patent: Aug. 9, 2016

(54) CONTAINER MANUFACTURING PLANT COMPRISING AN AIR RECYCLING CIRCUIT AND RECYCLING METHOD

(75) Inventor: Eric Adriansens, Octeville sur Mer (FR)

(73) Assignee: SIDEL PARTICIPATIONS, Octeville sur Mer (FR)

( * ) Notice: Subject to any disclaimer, the term of this patent is extended or adjusted under 35 U.S.C. 154(b) by 630 days.

(21) Appl. No.: 13/702,336

(22) PCT Filed: Jun. 8, 2011

(86) PCT No.: PCT/EP2011/059492
§ 371 (c)(1),
(2), (4) Date: Dec. 6, 2012

(87) PCT Pub. No.: WO2011/154447
PCT Pub. Date: Dec. 15, 2011

(65) Prior Publication Data
US 2013/0133297 A1   May 30, 2013

(30) Foreign Application Priority Data
Jun. 10, 2010   (FR) .................................. 10 54592

(51) Int. Cl.
*B65B 3/02*   (2006.01)
*B29C 49/46*   (2006.01)
(Continued)

(52) U.S. Cl.
CPC ................ *B65B 3/022* (2013.01); *B29C 49/46* (2013.01); *B29C 49/68* (2013.01); *B29C 49/06* (2013.01); *B29C 49/6418* (2013.01); *B29C 2049/4632* (2013.01)

(58) Field of Classification Search
CPC ........... F24F 2003/1628; F24C 15/327; B29C 49/46; B29C 2049/4697; B29C 49/42; B29C 49/68; B29C 2049/4632; B29C 49/06; B29C 49/6418; A61L 9/16; B65B 3/022
USPC .................... 425/210, 73, 526, 143; 454/187; 53/167, 558
See application file for complete search history.

(56) References Cited

U.S. PATENT DOCUMENTS 4,880,581 A * 11/1989 Dastoli et al. ................... 264/39
5,322,651 A   6/1994 Emmer
(Continued)

FOREIGN PATENT DOCUMENTS

EP   0 564 354   10/1993
EP   1699613   9/2006
(Continued)

OTHER PUBLICATIONS

International Search Report dated Jul. 20, 2011, corresponding to PCT/EP2011/059492.

*Primary Examiner* — Robert Long
*Assistant Examiner* — Xavier A Madison
(74) *Attorney, Agent, or Firm* — Young & Thompson (57) ABSTRACT

A recycling method and to a plant (10) for manufacturing containers (12) from thermoplastic preforms (14), is characterized in that the plant (10) includes a circuit (60) for recycling the cooling air from the oven (26) including: extraction elements (56), which are capable of extracting the filtered air injected into the interior of the oven (26) by an air-cooling device (34); and at least one duct (62, 74) capable of bringing all or part of the filtered air extracted from the oven (26) as far as at least one unit (38, 48) of the plant into which the air is injected.

17 Claims, 5 Drawing Sheets

(51) Int. Cl.
    *B29C 49/68*     (2006.01)
    *B29C 49/06*     (2006.01)
    *B29C 49/64*     (2006.01)

(56) References Cited

U.S. PATENT DOCUMENTS

| | | | |
|---|---|---|---|
| 5,714,109 | A | 2/1998 | Diller |
| 7,448,866 | B2 | 11/2008 | Doudement |
| 7,866,355 | B2 | 1/2011 | Quetel |
| 7,938,639 | B2 | 5/2011 | Adriansens |
| 8,257,073 | B2 | 9/2012 | Quetel |
| 2005/0129571 | A1* | 6/2005 | Centanni ................ 422/31 |
| 2009/0317506 | A1 | 12/2009 | Adriansens |
| 2010/0015269 | A1* | 1/2010 | Matsushita et al. ........ 425/143 |

FOREIGN PATENT DOCUMENTS

| | | |
|---|---|---|
| EP | 1982820 | 10/2008 |
| EP | 2191953 | 6/2010 |
| FR | 2899219 | 10/2007 |
| JP | 2008-207434 | 9/2008 |
| JP | 2010507503 A | 3/2010 |
| WO | 2005/070793 | 8/2005 |
| WO | 2008/049876 | 5/2008 |

* cited by examiner

CONTAINER MANUFACTURING PLANT COMPRISING AN AIR RECYCLING CIRCUIT AND RECYCLING METHOD

The present invention relates to a plant for manufacturing containers, comprising an air recycling circuit, and to a recycling method.

The present invention relates more particularly to a plant for manufacturing containers from thermoplastic preforms, comprising at least one protective enclosure intended to isolate an interior volume of the plant from the ambient air contained in an industrial premises in which the plant is installed, the plant comprising, arranged in said interior volume, at least:

- a unit for thermally conditioning the preforms which consists of an oven comprising heating means associated with an air-cooling device which comprises means of filtering the ambient air drawn from the industrial premises by ventilation means in order to cool at least part of the preforms in transit inside the oven using said filtered air;
- a unit for converting the preforms into containers, and
- a unit for filling the containers obtained from said preforms.

Production facilities comprising at least one building housing at least one industrial premises and such a container manufacturing plant installed in said premises, are known.

Plants of this type are intended for manufacturing containers, notably bottles, vials, etc., from preforms or parisons obtained beforehand by the injection molding of thermoplastic, particularly PET (polyethylene-terephthalate).

Such preforms are thermally conditioned beforehand in an oven that forms the thermal conditioning unit of the plant in order to allow them to be converted subsequently into a container in the next unit, notably by means of a blow-molding or stretch-blow-molding operation.

Control over the thermal conditioning step is achieved by the combined application to the body of cooling air and of infrared radiation emitted by the heating means over a given length of time. Air-cooling has the effect of encouraging radiative heating by moderating the effects of thermal conduction through the mass of air contained in the oven.

This is why the oven of a plant comprises an air-cooling device intended to subject at least the body of the preforms progressing through the oven to a stream of cooling air.

In addition to the ventilation means intended to establish said stream of cooling air within the heating zone of the oven, the cooling device comprises air filtration means.

Such air filtration means are intended to eliminate impurities (dust, micro-organisms, etc.) from the air so that the cooling air delivered to the preforms is a filtered air with the highest possible level of cleanliness.

The oven is also fitted with an air extraction system, such as an extraction hood, which comprises suction means associated with a discharge pipe for extracting said cooling air and discharging this air to the atmosphere.

Such an extraction system therefore allows heat energy resulting from the heating performed in the oven to be discharged together with the air.

In certain plants, such an extraction system also allows residual toxic vapors of sterilizing agent to be discharged when an operation of decontaminating the interior of the preforms by applying a sterilizing agent evaporated by heating in the oven is carried out at the same time as the thermal conditioning.

As a result, in the various plant designs known from the prior art, the ambient air drawn from the industrial premises in which the plant is installed and filtered by the filtration means of the cooling device with which the oven is equipped is then discharged to the atmosphere, notably via a discharge pipe of an extraction system, i.e. is discharged to outside the premises in which the plant is installed in order to remove both the heat and the residues of sterilizing agent.

However, the air consumption of such a cooling device in present-day plants is relatively high, the air flow rates being, for example, of the order of 20 000 to 30 000 $m^3$ per hour depending on the type of oven.

In order to gain a clear understanding of the magnitude of the ambient air consumption of such a cooling device, it can be revealed that the volume of air consumed by the cooling device in one hour of operation is generally greater than the volume of the industrial premises from which the device draws the ambient air.

Now, because "nature abhors a vacuum" (Aristotle's aphorism), the volume of air discharged to the atmosphere after cooling is immediately replaced in the industrial premises by an equivalent volume of air.

Thus, the ambient air contained in the industrial premises in which the plant is installed is being constantly renewed, generally with atmospheric air coming from outside the building of the production facility housing the premises and its plant.

However, the atmospheric air entering the industrial premises from outside has uncontrolled qualitative parameters.

In particular, the air temperature, its humidity or even the presence of undesirable bacteria and also dust are not controlled and are as many parameters that are universally acknowledged to have a direct influence on the quality of manufacture of the containers.

What is more, such parameters fluctuate according to the geographic location of the building containing the plant or even—for the same location—with the season which is liable to modify some of these qualitative parameters such as the air temperature (which can even vary over the course of one same day).

The problems presented are therefore the impact that these variations in the qualitative parameters (temperature, humidity, etc.) of the atmospheric air with which the ambient air in the industrial premises is renewed, especially the cleanliness (dust, bacteria, etc.) have on this air that leads to impaired quality of manufacture of the containers, and especially cleanliness of the containers.

In addition, a further consequence of this is that the filtration means of the cooling device become fouled, resulting in a reduction in the life of the filtration means and an increase in the frequency of maintenance operations, both of these requiring a full production shutdown.

This then has a direct economic impact on the container manufacturing plant operating costs.

In order to control the quality of the ambient air in the industrial premises it is possible to resort to converting the industrial premises into a "clean room" environment, i.e. an airtight space configured to eliminate as much dust and micro-organisms as possible in order to obtain ultra-clean industrial manufacturing conditions in the industrial premises.

However, it will be readily appreciated that while such a conversion remains possible, the associated costs, both for converting the industrial premises and later for operating the plant, are extremely and prohibitively high.

It is notably an object of the present invention to address the aforementioned disadvantages and to provide a plant that is particularly economical to run, while at the same time performing well in terms of the quality of the containers and advantageously being more ecologically sound.

To this end, the invention proposes a plant of the type described hereinabove, characterized in that the plant comprises a cooling-air recycling circuit comprising:

extraction means which are able to extract from the oven the filtered air introduced into the oven by the air-cooling device, and at least one pipe able to convey at least some of said filtered air extracted from the oven to at least one unit of the plant into which said air is introduced, by means of which all or some of said air filtered initially to perform air-cooling in the oven is recycled at least directly to the conversion unit and/or the filling unit.

Advantageously, a recycling circuit according to the invention allows the air filtered by the air-cooling device with which the oven is equipped to be recycled, i.e. allows the filtered air to be used again directly "in a loop" after it has been first used in the oven for cooling purposes.

Advantageously, the recycled cooling air has particularly advantageous qualities in relation to atmospheric air, which atmospheric air would, in a plant according to the prior art, have been admitted to the industrial premises in order to renew the air previously completely removed to the atmosphere.

Specifically, the cooling air undergoes at least one filtration operation as it passes through the filtration means of the cooling device which means that this air later recycled has, first and foremost, a particularly high degree of cleanliness, dust, bacteria, etc. having already been removed from it.

In addition, as it passes through the oven, the cooling air dries out under the effect of the heat prevailing inside the oven, which means that the air is dehumidified without having to resort to additional means.

Advantageously, the parameters of the ambient air of the premises are thus controlled, thereby improving the overall quality of the containers produced by the plant.

Advantageously, the industrial premises are provided with means of regulating the temperature of the ambient air which are able to keep the air temperature within a range of temperature values that ensure optimum manufacturing conditions.

Thanks to the recycling according to the invention, it is recycled air that is introduced into the filling unit and/or the conversion unit in place of the ambient air which previously also would have been drawn into the industrial premises by a blower system equipping each of these units.

Advantageously, the total air consumption of the plant is thereby considerably reduced since the cooling air recycled from the oven supplies the filling unit and/or the conversion unit directly as required in order to keep the interior volume of at least one unit at a raised pressure in order to avoid any contamination of the production means located therein.

Advantageously, the air consumption of the oven cooling device is in fact higher than that of the filling unit and of the conversion unit so that the recycling circuit completely provides for all of the air needed to achieve the raised pressure both in the filling unit and in the conversion unit.

Advantageously, the air recycled by the recycling circuit into at least one of the units of the plant is then exhausted to outside the enclosure to return to the industrial premises in which the plant is installed, thus renewing the ambient air drawn in by the cooling device.

The recycled air returned to the ambient air is therefore able to be used once again, and in particular drawn up once more by the cooling device and so on, in a looped circulation.

Because the step of discharging all of the cooling air to the atmosphere has been eliminated, the ambient air is no longer renewed with atmospheric air because the recycling circuit is returning air, advantageously filtered air, to the premises after it has been recycled through the plant.

Thanks to such recycling, the ambient air contained in the industrial premises is air the cleanliness of which increases with the time that the plant is kept running.

Indeed, the ambient air drawn by the oven cooling device from the industrial premises is cleaner on each of its passes through the filtration means comprising at least the filtration means of said device and, for preference, also the respective filtration means of the filling unit and/or of the conversion unit.

Advantageously, the cooling device and the means of the recycling circuit are therefore switched into operation for a given length of time before the actual manufacture of the containers begins, the purpose of this being to improve the quality of the ambient air contained in the industrial premises.

Thus, when the thermal conditioning of the preforms followed by the conversion into containers begins in the manufacturing plant, the ambient air which is drawn by the cooling device is air that is far cleaner because it has already been filtered for that determined length of time.

Advantageously, control over the quality of the ambient air, which is achieved through performing the recycling according to the invention, makes it possible to increase the manufacturing quality of the containers obtained with such a plant, especially the level of cleanliness of the containers, this being a quality criterion which is notably checked most rigorously in the context of agri-foodstuffs applications.

In addition, the fouling of the entirety of the filtration means with which the plant is equipped is thereby reduced and the life of these means is increased, to the benefit of a reduction in the associated running costs.

Advantageously, the recycling circuit according to the invention also makes it possible to achieve substantial economic benefits, notably as a result of the reduction in the frequency of maintenance or filtration-means-change operations and of the increase in the overall life of the filtration means.

According to other features of the manufacturing plant according to the invention:

the recycling circuit comprises a main pipe an upstream end of which is connected to the extraction means and a downstream end of which is connected to the filling unit so that at least some of the filtered air extracted from the oven is recycled by being introduced into said filling unit;

the recycling circuit comprises a branch pipe an upstream end of which is connected to the main pipe or to the extraction means and the downstream other end of which is connected to the unit that converts the preforms into containers so that at least some of the filtered air extracted from the oven is recycled by being introduced into said conversion unit;

the conversion unit and/or the filling unit comprise filtration means for filtering the air from the recycling circuit that is introduced into one and/or the other of the units so as to perform double filtration on the recycled air;

the recycling circuit comprises a discharge pipe, an upstream end of which communicates with the extraction means and the downstream other end of which opens into the atmosphere, outside the industrial premises, and regulating means are arranged so as selectively to distribute the extracted air into said discharge pipe and/or into said at least one pipe of the air recycling circuit;

with the plant comprising a module for decontaminating the preforms by applying at least one sterilizing agent, said decontamination module comprises extraction means able to suck up the air containing the sterilizing agent in the gaseous state from a sterilization chamber of the module so as to discharge from the module said air laden with sterilizing agent via at least one suction pipe the outlet of which is connected to the discharge pipe that opens into the atmosphere;

the decontamination module comprises extraction means which are separate from the extraction means of the recycling circuit which are intended to suck the filtered air out of the oven;

the recycling circuit comprises treatment means able to neutralize all or some of the sterilizing agent present in the recycled air;

the sterilizing-agent treatment means are arranged at least in the pipe able to convey all or some of said filtered air extracted from the oven to at least one unit of the plant;

sterilizing-agent treatment means are arranged in one and/or the other of said suction pipe and said discharge pipe in order to neutralize all or some of said sterilizing agent present in the air.

The invention also proposes a method for recycling air in a plant for manufacturing containers from preforms, comprising at least the steps which consist in successively:

a) filtering ambient air in order, using said filtered air, to air-cool at least part of the preforms while they are undergoing thermal conditioning in an oven of the plant;

b) extracting the filtered air from the oven after said air has been used for cooling;

c) recycling at least some of said filtered air extracted from the oven by introducing all or some of said air into a conversion unit and/or a filling unit of the plant.

Thanks to the air recycling method, it is possible to exercise control over the qualitative parameters of the ambient air and, in particular, the degree of cleanliness of the air and, therefore, incidentally, that of the containers manufactured, is increased.

Advantageously, the steps of the recycling method are implemented in a plant comprising a recycling circuit according to the teachings of the invention.

Further features and advantages of the invention will become apparent from reading the detailed description which will follow, for an understanding of which reference will be made to the attached drawings in which.

The entirely nonlimiting convention adopted in the description and the claims is "front" or "rear" with reference to the longitudinal direction, "upper" and "lower", with reference to the vertical direction and according to the earth's gravitational field, and longitudinal, vertical and transverse directions with reference to the trihedron (L, V, T) indicated in the figures.

The expressions "upstream" and "downstream" will be used with reference to the direction in which the stream of air circulates through the plant and/or the air recycling circuit.

Figure 1:
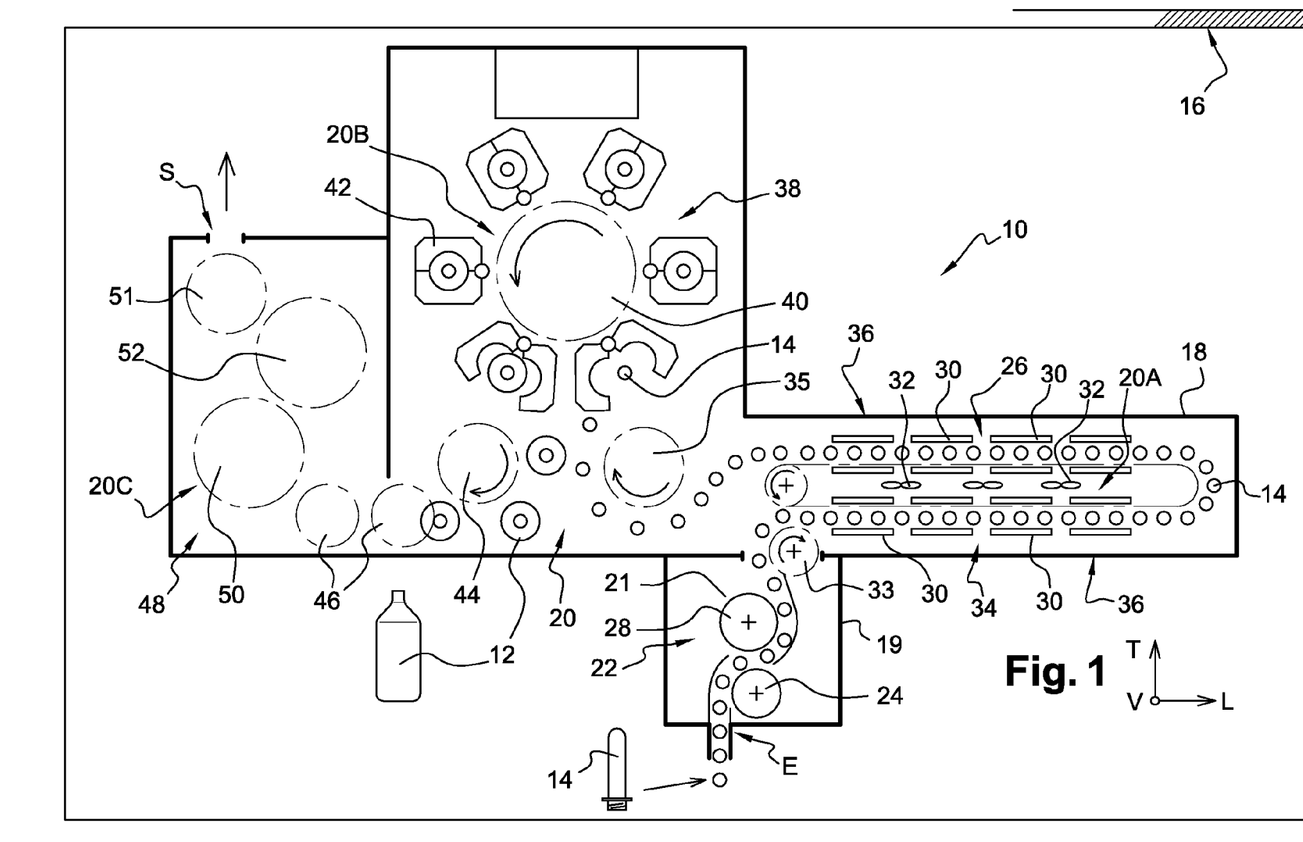
FIG. 1 is a schematic view from above partially depicting one example of a container manufacturing plant comprising a decontamination module and illustrating the state of the art for the applicant company.

FIG. 1 schematically depicts a plant 10 for the manufacture of containers 12 from a thermoplastic preform 14 which, nonlimitingly, illustrates one exemplary embodiment of a plant constituting the state of the art for the applicant company.

FIG. 1 depicts an example of a preform 14 for the manufacture of a container 12, forming a hollow body and notably intended to be thermally conditioned and then converted in order to obtain said container 12, such as a bottle, a vial, etc.

For preference, the operation of converting the thermally conditioned preform 14 is performed by blow-molding or stretch-blow-molding, although as an alternative it can be performed completely or partially by filling with a pressurized liquid able to form the container.

By definition, the term "container" in the remainder of this description denotes both the finished container obtained by a method of manufacture involving a single step of converting a preform that results directly in the finished container, such as the bottle illustrated in detail in FIG. 1, and an intermediate container obtained in the case where a method with multiple conversion stages is used.

The plant 10 is installed in an industrial premises 16, generally closed, located within a building (not depicted) of a production facility and which has a volume V of ambient air constituting a determined external environment around the plant 10.

Advantageously, the plant 10 comprises at least one plant protection enclosure 18 intended to isolate, with respect to said external environment formed by the industrial premises 16 in which the plant 10 is installed, an internal volume 20 within which the various means of manufacturing the containers 12 are arranged.

The plant 10 is associated with a system that feeds it with preforms 14. Such a feed system (not depicted) is, for example, described in document WO-2005/070793 to which reference can be made for the details.

Advantageously, the plant 10 depicted in FIG. 1 comprises a module 22 for decontaminating the preforms 14, notably by applying at least one sterilizing agent.

As an alternative, the plant 10 is, however, able to have no such decontamination module 22. For preference, the decontamination module 22 is therefore designed as a standalone device so that it can selectively be included within the plant 10 depending on the application.

At the lower end of rails of the feed system, the preforms 14 are picked up individually by a charging wheel 24 arranged at the entrance E of the plant 10.

Advantageously, the decontamination module 22 comprises a protective enclosure 19 which is separate from the overall enclosure 18 delimiting the interior volume 20 containing said manufacturing means of the plant 10.

The enclosure 19 that protects the decontamination module 22 also delimits an interior volume forming a sterilization chamber 21 in which the preforms 14 are treated with a sterilizing agent.

The plant 10 comprises a thermal conditioning unit consisting mainly of at least one oven 26.

Advantageously, the decontamination module 22 is positioned upstream of the oven 26 so that the entrance E is formed in the enclosure 19 that protects the decontamination module 22. As an alternative, the decontamination means are positioned downstream, notably after the exit from the oven 26.

For preference, the decontamination module 22 is able to spray a jet of dry vapor onto the preforms 14 so as to cause a uniform film of sterilizing agent mist to condense onto at least the internal wall of the preforms 14 that are to be sterilized.

Advantageously, the sterilizing agent applied by the decontamination module 22 in the state of dry vapor contains hydrogen peroxide ($H_2O_2$), for example as a mixture of water and hydrogen peroxide which is vaporized by means of vaporization means using heating (which have not been depicted) belonging to the decontamination module 22.

The decontamination module 22 for example comprises a sterilizing wheel 28 provided with means of supporting the preforms 14 by virtue of which means the preforms 14 travel neck uppermost under nozzles that apply the stream of dry sterilizing agent vapor that notably enters each preform 14 via the opening delimited by the neck.

Such a decontamination module 22 is described for example in document FR 2 899 219 to which reference may be made for a more detailed description of said device.

The preforms 14 are then transferred from the sterilizing wheel 28 of the decontamination module 22 to the oven 26 using a transfer wheel 33 and an opening formed in the protective enclosure 19.

The thermal conditioning unit of the plant 10 which is formed by the oven 26 chiefly comprises heating means 30 and associated ventilation means 32 for thermally conditioning the preforms 14.

Advantageously, the oven 26 comprises a cooling device 34 which, associated with the heating means 30, respectively comprises filtration means 36 and said ventilation means 32.

On entering the oven 26, the preforms 14 are transferred from the wheel 33 to a conveyor device (not depicted), such as an endless chain bearing means of supporting the preforms 14 and intended to transport them in a set heating path ending at the exit from the oven 26, for example in this instance a U-shaped path comprising two parallel longitudinal heating legs, one outbound, the other return, joined together by a transverse curved portion known as the stabilizing portion.

For preference, the support means of the conveying device are able to rotate each preform 14 on itself in order to encourage a suitable distribution of heat through the body of each preform 14.

Document EP 1 699 613 describes an example of an oven comprising heating means 30 and ventilation means 32 for thermally conditioning preforms.

Advantageously, the oven comprises sterilizing means that work by emitting ultraviolet radiation and are arranged at least in the curved stabilizing portion as described in document WO-2008/049876.

Once they have been thermally conditioned in the oven 26, the preforms 14 are transported by at least one transfer wheel 35 from the exit of the oven 26 to a unit 38 that converts the preforms 14 into containers 12.

Advantageously, the conversion unit 38 here consists of a blow-molding machine known as a blow molder.

In the example depicted in FIG. 1, the blow-molding machine is of the rotary type and comprises a carousel 40 equipped with a plurality of workstations which are circumferentially distributed and each mainly provided with molding means 42 and with associated blowing or stretch-blowing means (not depicted).

For preference, the containers 12 obtained are then transported, for example by transfer wheels 44, 46, to a filling unit 48.

Advantageously, the filling unit 48 comprises at least one filling machine 50 and preferably also a stoppering machine 52, said machines 50, 52 (not depicted in detail) being able successively to fill the containers 12 and then to close the filled containers 12, for example using screw caps that complement the necks.

For preference, the filling unit 48 is juxtaposed with the conversion unit 38 in order to obtain a compact plant 10 in which the entire manufacturing process is carried out until filled and sealed, and even labeled containers 12 are ultimately obtained.

The containers 12 are, for example, conveyed toward an exit S by a transfer wheel 51 and can then be packaged, notably batched, wrapped and palletized, for dispatch for marketing purposes.

As illustrated in FIG. 1, the enclosure 18 of the plant 10 delimits an overall interior volume 20 in which all of the manufacturing means 26, 38, 48 just described are located and which are thus confined and isolated from the external environment.

By convention, in the description that follows, the interior volume 20 will be divided into several interior volumes 20a, 20b and 20c delimited by a corresponding part of the enclosure 18 and associated with each of the units, namely with the thermal conditioning unit i.e. the oven 26, with the conversion unit 38 and with the filling unit 48, respectively.

The enclosure 18 (embodied by a thick outline in FIG. 1) consists for example of a collection of vertical walls made up of panels and of at least one horizontal wall to form a ceiling covering the entire plant 10.

The operation and circulations of air that occur between the ambient air contained in the industrial premises 16 and the plant 10 installed therein will now be described with reference to FIG. 2.

The plant 10 comprises an air extraction system 54 which, combined with the oven 26, comprises air extraction means 56 intended to extract the cooling air from said interior volume 20A delimited by that part of the enclosure 18 that surrounds the oven 26, the reason for this being to discharge said air to the atmosphere in the way explained hereinabove.

In such a plant 10, the circulation of air in the oven 26 begins with the intake of ambient air which is drawn from the industrial premises by the ventilation means 32 of the cooling device 34.

For preference, the air is filtered by the filtration means 36 as it enters the oven 26.

Figure 2:
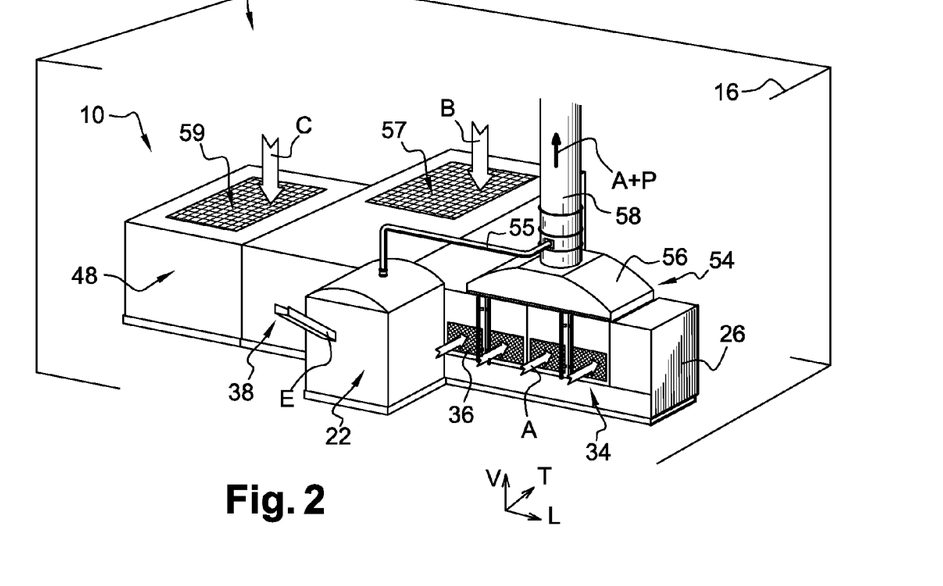
FIG. 2 is a perspective view schematically depicting a plant according to FIG. 1.

The corresponding air stream is illustrated in FIG. 2 by arrows "A" in the vicinity of the intake openings for the air intended for cooling at least part of the preforms.

Inside the oven 26, the filtered air is conveyed to the zone in which the preforms 14 are heated, where in particular it comes into contact with the bodies of the preforms 14 in order to cool them.

The cooling air is then extracted from inside the oven 26 by the air extraction means 56 of the system 54 so that it can be completely discharged by a discharge pipe 58 to the atmosphere, namely outside the building containing the industrial premises 16 installed therein.

When the plant 10 comprise a decontamination module 22, the extraction system 54 also discharges into the atmosphere the air laden with sterilizing agent that has been extracted from the sterilizing chamber 21 and which is symbolized by the letter "P" in FIG. 2.

To do that, the decontamination module 22 comprises a suction pipe 55 connected to the discharge pipe 58 opening into the atmosphere which therefore discharges the air laden with sterilizing agent from the decontamination module 22 and the cooling air from the oven 26.

Thanks to such an air extraction system 54, the heat produced by the oven 26 on the one hand, and, in the case of a plant 10 comprising a decontamination module 22, the sterilizing agent present in the gaseous state in the air, on the other hand, are discharged with the air.

Advantageously, an air blowing system 57 is associated with the conversion unit 38 which here comprises a blow-molding machine, said system 57 being incorporated into an upper part of the enclosure 18, forming a ceiling.

This blowing system 57 is intended to blow air into the associated part of the interior volume 20B isolated from the external environment, the purpose of this being to establish therein a raised pressure that allows an effective reduction in the risks of contamination from the outside, notably by airborne particles.

The blowing system 57 therefore draws from the industrial premises 16 a given volume of ambient air which is symbolized by the arrow "B" in FIG. 2.

A similar air blowing system 59 is fitted to the filling unit 48 in order likewise to establish a raised pressure within the interior volume 20C delimited by the enclosure 18, the ambient air drawn from the industrial premises 16 by the blowing system 59 being symbolized by an arrow "C" in FIG. 2.

By way of nonlimiting examples, the air consumption or air flow rate drawn in by a blowing system 57 is of the order of 8000 $m^3$ per hour, while that of the blowing system 59 is of the order of 10 000 $m^3$ per hour.

Greater still is the air consumed by the air-cooling device 34 associated with the oven 26 because that for example reaches values of the order of 20 000 to 30 000 $m^3$ per hour depending on the type of oven, and particularly on the number of heating modules.

For an oven 26 of modular design, the air consumption per heating module is of the order of 1300 $m^3$ per hour, it being possible for the oven to comprise for example 20 modules.

As explained previously, the amount of ambient air drawn from the industrial premises 16 by the cooling device 34 and its subsequent discharge to the atmosphere cause a massive intake of atmospheric air into the industrial premises 16 in order to compensate for the cooling air discharged by the discharge pipe 58 of the extraction system 54.

Now, renewing ambient air with atmospheric air leads to a significant variation in the qualitative parameters of the air (temperature, humidity, cleanliness, etc.) with a direct impact on the manufacturing process, especially the thermal conditioning.

Above all, a lack of cleanliness (presence of dust, microorganisms, etc.) of the atmospheric air impairs the quality of the containers 12 manufactured.

In addition, it also leads to premature fouling of the filtration means 36 of the cooling device 34.

One of the consequences of this is that it reduces the life of the filtration means and increases the frequency of maintenance operations requiring a complete production shutdown, failure to perform which has a direct impact on the degree of cleanliness of the containers 12 manufactured which soon degrades.

The negative impact therefore has as much of an impact on the cost of operating the container manufacturing plant 10 as it does on the degree of cleanliness of the containers 12 manufactured.

With a view notably to addressing these disadvantages, the invention proposes to recycle the cooling air extracted from the oven in order to dispense with the need to renew ambient air with atmospheric air, while at the same time advantageously benefiting from the fact that this air is filtered air so as to improve the quality of the containers manufactured, especially the degree of cleanliness.

To do this, the invention proposes a method for recycling air in a plant 10 for manufacturing containers 12 from preforms 14, comprising at least the steps which consist in successively:

a) filtering ambient air in order, using said filtered air, to air-cool at least part of the preforms 14 while they are undergoing thermal conditioning in an oven 26 of the plant 10;

b) extracting the filtered air from the oven 26 after said air has been used for cooling;

c) recycling at least some of said filtered air extracted from the oven 26 by introducing all or some of said air into a conversion unit 38 and/or a filling unit 48 of the plant 10.

According to the recycling method according to the invention, the air filtered by the cooling device is recycled, i.e. is preferably introduced directly into at least one of the units 38, 48 of the plant 10 in such a way as to be used once again as ambient air.

Advantageously, in the case of direct discharge into at least one unit 38, 48, the recycling of the cooling air makes it possible to put an end to the practice of renewing air with atmospheric air which was hitherto employed in plants in which this air was discharged to the atmosphere.

Specifically, the air recycled by the recycling circuit into at least one of the units of the plant then escapes to outside the enclosure to return to the industrial premises in which the plant is installed where it can once again be used by the cooling device 34.

Thanks to the invention, the ambient air contained in the industrial premises 16 is an air the cleanliness of which will increase with the length of time for which the plant 10 is running, dust, bacteria, etc. being removed by the successive filtration operations.

Advantageously, the control exercised over the quality of the ambient air as a result of performing the recycling according to the invention makes it possible to increase the quality of manufacture of the containers obtained using such a plant, especially the degree of cleanliness.

A first preferred embodiment and a second preferred embodiment of the invention, which respectively illustrate how the recycling method is used in a plant 10 for manufacturing containers 12, will now be described by way of nonlimiting examples.

According to the invention, the plant 10 comprises a cooling-air recycling circuit 60 comprising:

extraction means 56 which are able to extract the filtered air introduced into the oven 26 by the air-cooling device 34, and at least one pipe able to convey at least some of said filtered air extracted from the oven 26 to at least one unit 38, 48 of the plant into which said air is introduced, by virtue of which all of some of said air filtered initially in order to perform air-cooling in the oven 26 is recycled at least to the conversion unit 38 and/or the filling unit 48.

Advantageously, the recycling circuit 60 comprises at least one pipe 62, 74 of which an upstream end is connected to extraction means 56 and of which the downstream other end is connected to one of the units 38, 48.

Thanks to the recycling circuit 60 according to the invention, the ambient air initially filtered by the filtration means 36 to perform cooling in the oven 26 is recycled into at least one unit of the plant 10, such as the conversion unit 38 and/or the filling unit 48.

Advantageously, the air filtered for cooling purposes is therefore no longer discharged into the atmosphere but used again in the plant 10.

The first effect of the recycling according to the invention is to eliminate the demand for air which previously caused atmospheric air to enter the industrial premises 16 to compensate for the air discharged into the atmosphere.

Advantageously, variations in the qualitative parameters of the air in the industrial premises 16, particularly cleanliness, are limited.

Specifically, the recycled air is restored indirectly to the industrial premises 16 having for example passed through the filling unit 48 of which the interior volume 20C is kept at a raised pressure inside the enclosure 18.

Because the filtered air is recycled into at least one unit to which it is introduced by the pipe of the recycling circuit 60, a second effect is that there is therefore no longer any need to draw, from the ambient air of the industrial premises 16, the air which previously had been necessary to create the raised pressure in said at least one unit 38, 48, i.e. with reference to FIG. 2, the airstream corresponding to arrow B and/or to arrow C.

Specifically, the air needed to create the raised pressure in the interior volume 20B of the conversion unit 38 and/or the interior volume 20C of the filling unit 48 is advantageously made up completely of recycled air delivered by the air recycling circuit 60.

Advantageously, because the recycled air has been filtered by the filtration means 36, the air delivered by the circuit 60 is air that has a degree of cleanliness which, having been determined by the filtration means used, is better than the initial degree of cleanliness of the ambient air.

For preference, the filtration means 36 of the cooling device 34 consist of filters known as "absolute" filters, such as filters of the ULPA or even of the HEPA type.

It will be recalled that "ULPA" is the acronym for an "Ultra Low Penetration Air" filter and that an "HEPA" filter is a "High Efficiency Particulate Air" filter.

Figure 4:
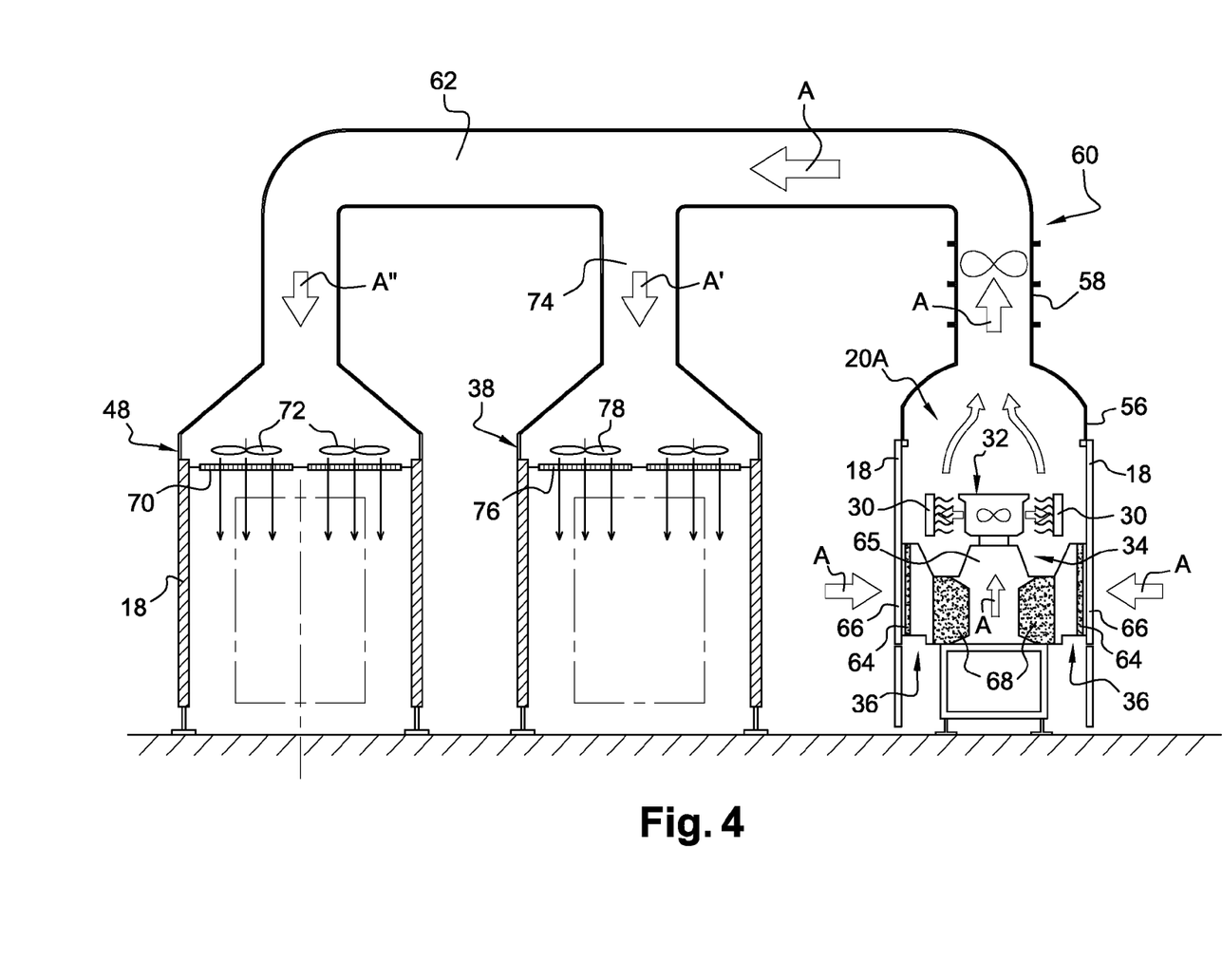
FIG. 4 is a view in cross section of the units of the plant according to FIG. 3, the oven being in transverse cross section and the other units in longitudinal section, and illustrating the recycling circuit according to the first embodiment.

For preference, and as illustrated in the transverse cross section of the oven 26 in FIG. 4, the filtration means 36 comprise a prefilter 64 positioned near an inlet 66 arranged in the enclosure and a filter 68 arranged in the vicinity of a downstream orifice of the inlet 64, the bore section of the prefilter 66 being greater than the bore section of the filter 68.

For preference, the prefilter 64 is a gravimetric filter capable of filtering what are known as coarse particles, of a given diameter, for example greater than ten microns.

Advantageously, the filter 68 is an "absolute" filter of one of the abovementioned types, capable of filtering what are known as fine particles, for example of a diameter greater than one micron.

Figure 3:
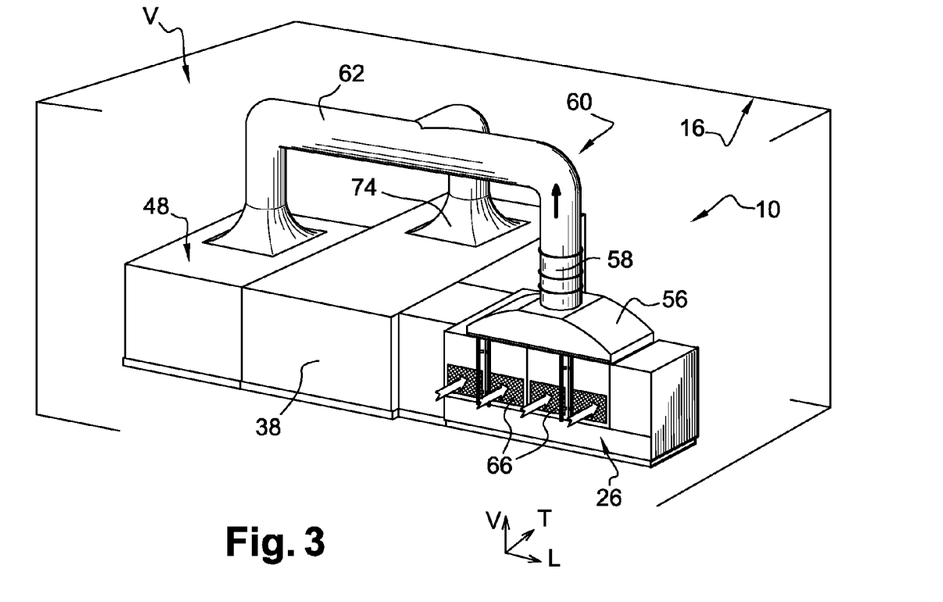
FIG. 3 is a perspective view depicting a manufacturing plant similar to that of FIGS. 1 and 2 with the exception of the absence of a decontamination module and which illustrates a first embodiment of a cooling-air recycling circuit according to the invention.

In the first embodiment of the invention which is depicted in FIGS. 3 and 4 and which will be described hereinafter by comparison, the plant 10 differs from the one described earlier with reference to FIGS. 1 and 2 in that it comprises no decontamination module 22.

Therefore, the filtered air recycled using the recycling circuit 60 according to the first embodiment is air completely free of sterilizing agent.

In this first embodiment, the recycling circuit 60 advantageously allows air to be recycled to the filling unit 48 and to the conversion unit 38.

As an alternative, the recycling circuit 60 allows air to be recycled to just one unit, either the filling unit 48 or the conversion unit 38.

The recycling circuit 60 comprises a pipe 62, termed the main pipe, so that at least some of the filtered air extracted from the oven 26 is recycled by being introduced into said filling unit 48.

For preference, the main pipe 62 has an upstream end connected to the extraction means 56 and a downstream other end connected to the filling unit 48.

The recycling circuit 60 comprises a pipe 74, known as a branch pipe, so that at least some of the filtered air extracted from the oven 26 is recycled by being introduced into said conversion unit 38.

For preference, the branch pipe 74 has an upstream end connected to the main pipe 62 and a downstream other end connected to the unit 38 that converts the preforms 14 into containers 12.

As an alternative, the branch pipe 74 has an upstream end connected to the extraction means 56 and a downstream other end connected to the unit 38 that converts preforms 14 into containers 12.

In this alternative form, the pipe 74 is then the only pipe in the circuit 60 which means that recycling is only to the unit 38 that converts the preforms 14 into containers 12.

For preference, the filling unit 48 comprises filtration means 70 which are interposed between a downstream end of the main pipe 62 and the interior volume 20C of the filling unit 48 which volume is delimited by part of the protective enclosure 18.

Advantageously, the filtered air introduced into the filling unit 48 is doubly-filtered air when this air is filtered first of all by the filtration means 36 of the cooling device 34 and then for a second time by the filtration means 70 associated with the filling unit 48.

For preference, the filling unit 48 comprises ventilation means 72 able to create a depression and a demand for filtered air circulating along the main pipe 62 in order partially to compensate for the pressure drops and guarantee an air flow rate capable of keeping the interior volume 20C at a raised pressure.

Advantageously, part of the recycled air circulating through the main pipe 62 is diverted to the branch pipe 74, here connected to the main pipe 62, so as to divert some of the air to the conversion unit 38 so that the recycled air is split between the filling unit 48 and the conversion unit 38.

This then establishes a raised pressure in the interior volume 20B of the filling unit 38.

Advantageously and as illustrated in FIG. 4, the conversion unit 38 comprises filtration means 76 and ventilation means 78 analogous with those of the filling unit 48.

Thanks to such filtration means 76, the recycled air introduced into the conversion unit 38 that will come into contact with the preforms 14 or the containers 12 is likewise double-filtered which means that these preforms or containers are kept in a controlled environment that makes it possible to maintain a very high degree of cleanliness.

Advantageously, the ventilation means 78 make it possible to guarantee that the raised pressure will be created in the interior volume 20B and to compensate for any potential pressure drop in the recycling circuit 60.

Advantageously, the conversion unit 38 and/or the filling unit 48 comprise filtration means 76, 70 for filtering the air from the recycling circuit 60 that is introduced into one and/or the other of the units 38, 48 so as to perform double filtration on the recycled air.

As an alternative, the conversion unit 38 and/or the filling unit 48 have no such filtration and ventilation means and the recycled air is introduced directly into the interior volume 20B and/or 20C.

Advantageously, the recycling circuit 60 according to the invention therefore allows both the filling unit 48 and the conversion unit 38 to be supplied with air in order respectively to establish a raised pressure in the interior volumes 20B, 20C of each of said units 38, 48.

By way of an alternative that has not been depicted, the recycling circuit 60 supplies air to just one unit, for example the filling unit 48.

The conversion unit 38 is then not connected and the branch pipe 74 is omitted. Advantageously, said conversion unit 38 then comprises air blowing means 57 able to establish a raised pressure in the interior volume 20C.

Of course, and by reciprocity, the recycling circuit 60 could supply only the conversion unit 38 via the pipe 74, the main pipe 62 then being omitted but blowing means 59 employed.

Thanks to the invention, when the air is recycled to both units 38 and 48, there is then no longer any need to draw from the ambient air of the industrial premises 16, and this too contributes to eliminating the ingress of atmospheric air into the industrial premises 16.

Indeed, only the cooling device 34 then draws ambient air contained in the industrial premises 16, said drawn ambient air being compensated for in the industrial premises 16 by the recycled air restored continuously by each of the units, conversion unit 38 and filling unit 48, at a raised pressure.

Advantageously, the ambient air drawn by the cooling device 34 is successively filtered twice, respectively in the cooling device 34 and then during recycling by the units 38, 48 so that the degree of cleanliness of the air ultimately returned to the industrial premises 16 after just one "loop" is already very much better than it was initially.

Indeed, once returned to the industrial premises 16, this air forms some of the ambient air and can therefore be drawn up once again by the cooling device 34.

It will be appreciated therefore that each time the air passes or loops through the recycling circuit 60 of the plant 10, the air returned at the outlet is air of increasing cleanliness.

This is why the recycling of the air carried out in accordance with the teachings of the invention makes it possible to improve the quality of the manufactured containers 12 which thus have a particularly high degree of decontamination or of sterility.

Advantageously, the recycling of the cooling air according to the invention makes it possible to reduce the fouling of the filtration means 36 and of the filtration means 70, 76 of the units 48, 38 and to reduce the frequency of maintenance interventions.

The quality of the ambient air is appreciably improved when the air is filtered by the filtration means or automatically dehumidified by the heating means 30 of the oven 26.

The operation of a recycling circuit 60 according to the first embodiment of the invention will now be described with reference to FIG. 4.

The ambient air is drawn from the industrial premises 16 by the cooling device 34 associated with the oven 26 and intended to air-cool at least part of the preforms 14.

More specifically, the ventilation means 32 suck in ambient air via the inlets 66 and cause a depression, preferably in a plenum 65. The ambient air thus sucked in will therefore be filtered by the filtration means 32 of the device 34, for example successively filtered by a prefilter 64 and then by a filter 66 positioned downstream of the prefilter 64.

From the plenum 65 that forms a reservoir of cooling air in the lower part of the oven 26, the filtered air is then sucked by the ventilation means 32 arranged in the heating zone so as to blow the cooling air, generally through reflectors, into said zone comprising the means 30 that heat the preforms 14.

The ventilation means 32 consist, for example, of a bucket wheel capable of propelling the cooling air into the heating zone at least toward the bodies of the preforms 14 in the process of being thermally conditioned.

After that, the cooling air is extracted from the top by the extraction means 56 of the air recycling circuit 60 according to the invention.

As depicted in FIG. 4, the arrows A illustrate in succession the path followed by the cooling air up to the point of its extraction by the extraction means 56 positioned above the oven 26, the extraction means 56 closing at the top the interior volume 20A that is delimited by part of the enclosure 18.

The filtered air thus extracted is then recycled via the circuit 60 which carries at least some of the air.

On the one hand, a first proportion of the air, represented by the arrow A', is conveyed as far as the conversion unit 38 by the main pipe 62 and the branch pipe 74 and, on the other hand, the other proportion corresponding to the arrow A" is conveyed to a filling unit 48 by the main pipe 62.

As an alternative, all of the recycled air stream depicted by the arrow A is introduced into the filling unit 48 or into the conversion unit 38.

The first proportion of this air that has reached the conversion unit 38 following arrow A' is then filtered a second time by the filtration means 76 with which the unit 38 is equipped and introduced into the associated interior volume 20B in order always to maintain a raised pressure in this corresponding part of the enclosure 18.

Advantageously, the ventilation means 78 cause suction in the branch pipe 74 in order to keep a high air circulation flow rate and maintain the raised pressure in the conversion unit 38.

The second portion of the air that has reached the filling unit 48 following the arrow A", advantageously with the assistance of the ventilation means 72, is then filtered a second time by the filtration means 70 with which the unit 48 is equipped and introduced into the associated interior volume 20C in order constantly to maintain a raised pressure in the enclosure 18 around the machines 50 and 52.

The air then escapes from the conversion unit 38 and from the filling unit 48 via the lower part of the enclosure 18, here near ground level, so that this air is then returned to the industrial premises 16.

According to the teachings of the invention, the air thus recycled prevents atmospheric air from penetrating the industrial premises 16 and makes it possible to ensure ambient air of high quality, in particular exhibiting a high degree of cleanliness.

Specifically, thanks to the recycling, the renewal of ambient air with atmospheric air is eliminated which means that the abovementioned disadvantages are likewise eliminated.

In order to obtain a clear understanding of the advantages of the invention, the air consumptions or air flow rates of a manufacturing plant 10 of the type described with reference to FIGS. 1 and 2 will be detailed hereinbelow.

The overall air consumption of a plant 10 is of the order of 30 000 to 50 000 m$^3$ per hour with the following overall distribution: around 20 000 to 30 000 m$^3$ for the air-cooling device 34 of the oven and 8000 to 12 000 m$^3$ for the blowing system 57 of the conversion unit 38, and for the blowing system 59 of the filling unit 48 which is generally around 8000 m$^3$ per hour.

To illustrate the magnitude of such air consumptions, it is beneficial to make a comparison with the overall volume of the industrial premises 16 in which the plant 10 is installed.

Thus, by way of nonlimiting example, if we consider industrial premises 16 of parallelepipedal overall shape, measuring respectively 6 m in height, 15 m in width and 30 m in length, we then get a volume of 2700 m$^3$.

The volume of 2700 m$^3$ of ambient air in the industrial premises 16 constitutes a "reservoir" from which the air needed by the plant 10 is drawn, both by the cooling device 34 and by the blowing means 57, 59, to raise the pressure in the units 38, 48.

Considering an air consumption of 27 000 m$^3$ per hour for the cooling device 34 alone, the air from which is discharged into the atmosphere, that means that the ambient air contained in this volume of industrial premises 16 will be renewed over ten times in the course of one hour with air taken from the atmosphere in order to compensate for the air removed.

The scale of the problems with the qualitative parameters which are associated with renewing the air with atmospheric air will therefore be readily understood as will the very significant impact this has on the quality of manufacture of the containers, notably by disrupting the thermal conditioning in the oven 26.

In a plant 10 comprising a recycling circuit 60 according to the invention, by eliminating the removal of the cooling air to the atmosphere, the volume V of the industrial premises 16 is going to be renewed with recycled air that becomes increasingly clean.

Advantageously, the recycled air is reused directly in the filling unit 48 and in the conversion unit 38 of the plant 10, preferably also establishing double filtration.

As an alternative that has not been depicted, the recycling circuit 60 according to the first embodiment comprises a discharge pipe for selectively diverting at least some of the extracted air and only partially recycling to at least one unit of the plant.

For preference, such a discharge pipe is similar to the pipe 58 of FIG. 2 and has an upstream end communicating with the extraction means 56 and a downstream other end which opens into the atmosphere, outside the industrial premises 16.

Advantageously, means for regulating the stream or flow are then fitted so that they can selectively control the distribution of extracted air to the main pipe 62 and/or said discharge pipe.

Figure 5:
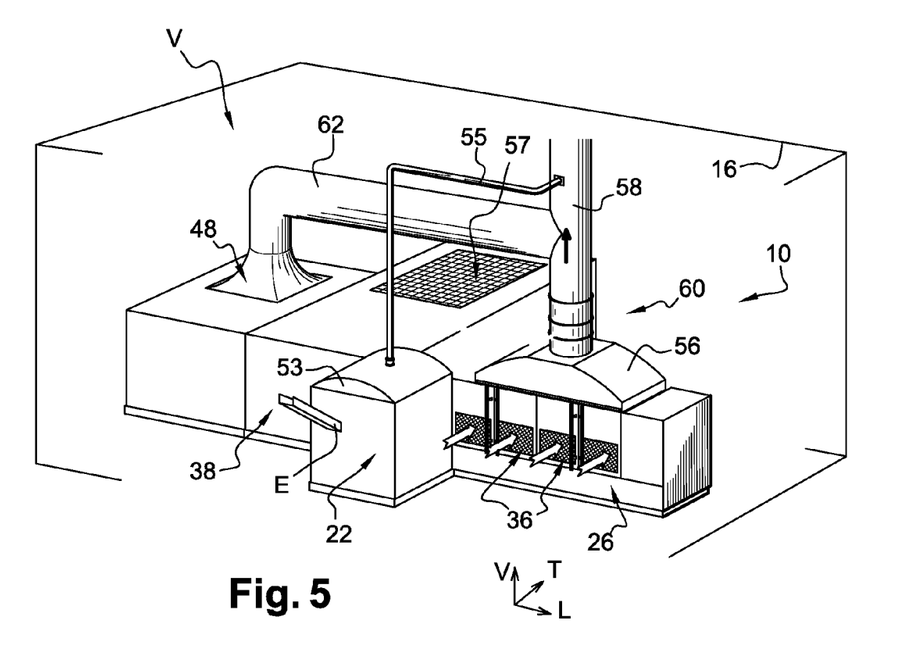
FIG. 5 is a perspective view schematically depicting a manufacturing plant similar to that of FIGS. 1 and 2 and comprising a preform decontamination module and illustrating a second embodiment of a cooling-air recycling circuit according to the invention.
Figure 6:
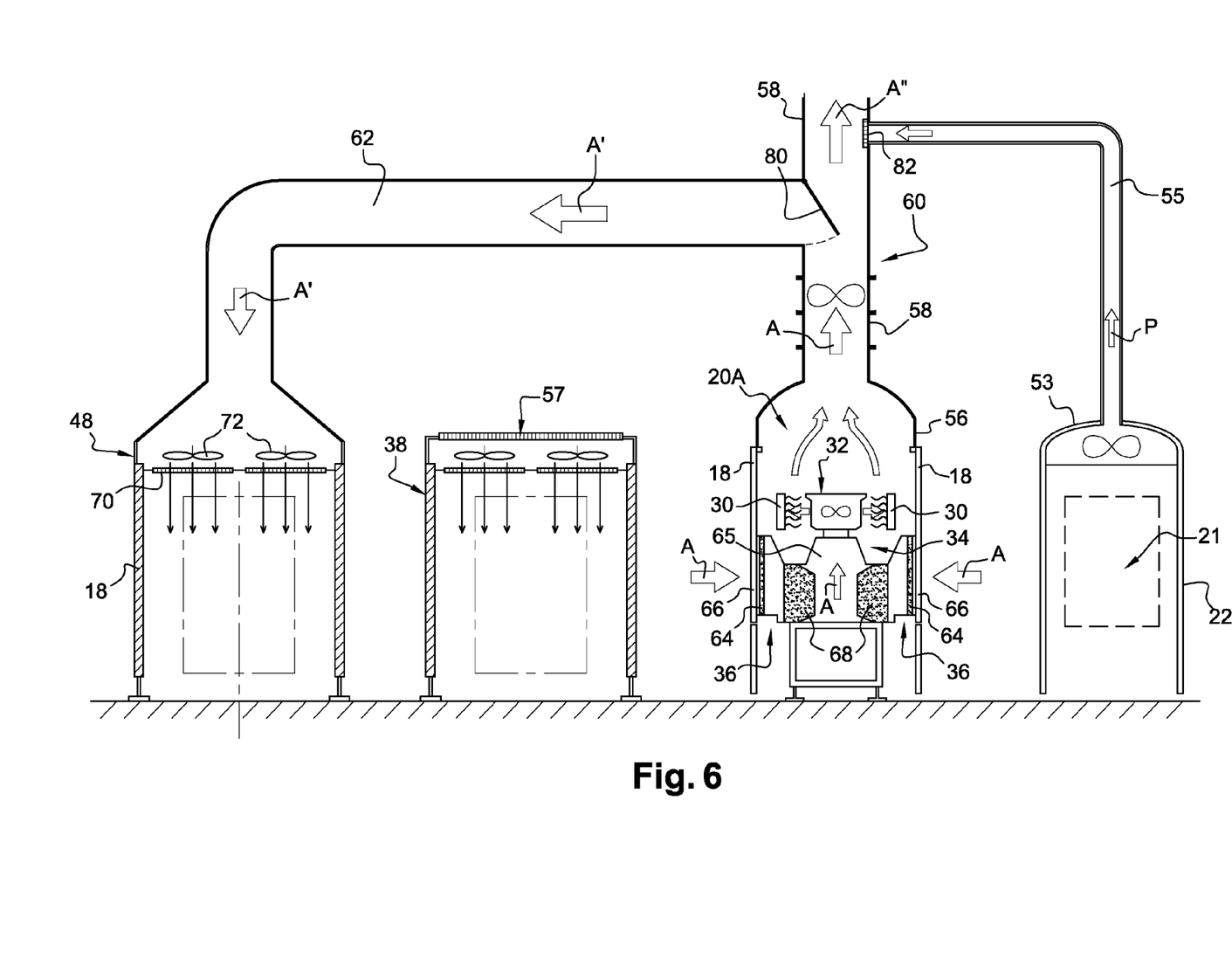
FIG. 6 is a view in cross section of the units of the plant according to FIG. 5, the oven being depicted in transverse cross section and the other units in longitudinal section with the decontamination module offset for the sake of the clarity of the drawing, the whole illustrating the recycling circuit according to the second embodiment.

A second embodiment of the invention respectively illustrating the implementation of the recycling method according to the invention in a plant 10 for manufacturing containers 12 that comprises a decontamination module 22 will now be described by way of comparison with the first embodiment.

The decontamination module 22 is similar to the one described previously with reference to FIGS. 1 and 2, notably in that it is advantageously able to decontaminate the preforms 14 by condensing onto them sterilizing agent that has been sprayed in the form of a stream of dry vapor.

Advantageously, the decontamination module 22 comprises extraction means 53 able to suck out the air containing the sterilizing agent in the gaseous state from the sterilizing chamber 21 of the decontamination module 22.

The decontamination module 22 comprises at least one suction pipe 55 for removing from the sterilizing chamber 21 said air laden with sterilizing agent which is sucked out by the extraction means 53.

For preference, the extraction means 53 are separate from the extraction means 56 associated with the oven 26.

Like in the first embodiment, the cooling-air recycling circuit 60 comprises extraction means 56, such as a hood, to extract from the interior volume 20A of the oven 26 the cooling air that has already been filtered by the filtration means 36 of the cooling device 34 and comprises a main pipe 62 able to convey the extracted air in order to recycle it.

In this second embodiment, the air is preferably recycled only to the filling unit 48, the reason for this being that there is a sterilizing agent present in this air.

Indeed it will be recalled that the sterilizing agent is evaporated in the oven 26 by the heating means 30 so that the air extracted contains sterilizing agent in the gaseous state, albeit in relatively low concentrations.

However, the quantity of sterilizing agent used with a condensing decontamination module 22 is advantageously lower by comparison with the earlier techniques of wetting or spraying with a liquid solution.

Because sterilizing agent is present in the recycled air and because of the generally corrosive nature of this type of agent, such as hydrogen peroxide, the air is not introduced into the conversion unit 38.

As an alternative, the recycled air could, however, be introduced into the conversion unit 38 by using appropriate treatment means capable of completely neutralizing the sterilizing agent present in the air before it is introduced into the conversion unit 38.

Advantageously, the air recycled by the circuit 60 has an even further enhanced degree of sterility due to the fact that, in addition to the filtration operation or operations that it has undergone, the sterilizing agent present in the air has a sterilizing effect notably as a result of its bactericidal properties.

By contrast, the presence of sterilizing agent in the air recycled to the filling unit 48 is advantageous.

This is because the filling unit 48 is usually considered to be that unit of the plant 10 to which greatest attention is paid with regard to the risk of pollution or contamination in order to guarantee the end quality of the containers 12 manufactured.

Moreover, the filling 50 or stoppering 52 machines of the filling unit 48 are generally made of stainless materials, such as stainless steel, so as to allow the unit 48 to undergo decontamination treatments likewise using a sterilizing agent.

This is why the presence of sterilizing agent in the recycled air carries no risk of corrosion to these machines 50, 52 and other means contained within the filling unit 48.

Advantageously, the recycled air laden with sterilizing agent will make it possible to sterilize the filtration means 70 of the filling unit 48 as it passes through these means, by virtue of which a sterilizing action is performed on said filtration means 70, the original sterility of the filtration means 70 thereby being extended through the presence of sterilizing agent in the recycled air.

The result of this is further to improve the cleanliness of the containers 12 manufactured.

For preference, treatment means capable of neutralizing the sterilizing agent present in the recycled air are incorporated into the recycling circuit 60 to guarantee that the sterilizing agent concentration in the recycled air remains below a set threshold value.

Such treatment means are, for example, arranged upstream of the filtration means 70, or as an alternative, in the main pipe 62.

Advantageously, the treatment means of the recycling circuit 60 comprise at least one oxidizing element capable of causing a catalytic reaction during which all or some of the sterilizing agent present in the extracted air is broken down into other, neutral, products.

For preference, the oxidizing agent consists of a compound containing platinum, silver or any other metal suited to performing catalysis.

When the sterilizing agent used is advantageously hydrogen peroxide, the latter is then broken down into water and molecular oxygen, namely products that are not at all harmful.

For preference, the treatment means consist of at least one filter containing at least said oxidizing element intended to interact with the sterilizing agent present in the extracted air, for example a filter provided with an active substrate comprising said oxidizing element.

For preference, the recycling circuit 60 comprises a discharge pipe 58 similar to that of FIG. 2, and comprises an upstream end which communicates with the extraction means 56 and a downstream other end which opens into the atmosphere, outside the industrial premises 16 notably in order to discharge some of the cooling air without recycling all of it.

Advantageously, means 80 of regulating the flow are arranged in such a way as selectively to control the distribution of extracted air in the main pipe 62 and/or in said discharge pipe 58.

By way of example, the regulating means 80 consist of a flap mounted such that it can move between at least one first extreme position in which the flap extends horizontally to close off the inlet to the discharge pipe 58, and a second extreme position in which the flap extends vertically to close off the inlet to the main pipe 62 of the recycling circuit 60.

Advantageously, the flap is able to occupy one or more intermediate positions between said extreme positions so as to distribute the extracted filtered air between the pipes 58, 62.

For preference and as illustrated in FIG. 5, the outlet of the suction pipe 55 of the decontamination module 22 is connected to the discharge pipe 58 of the recycling circuit 60 in such a way that the air laden with sterilizing agent extracted by the extraction means 53 from the sterilizing chamber 21 is discharged directly into the atmosphere.

Advantageously, the outlet of the suction pipe 55 is connected to the discharge pipe 58 downstream of the main pipe 62 and of the regulating means 80.

By way of nonlimiting example, the flow rate of air sucked by the extraction means 53 of the decontamination module 22 is of the order of 600 to 800 m$^3$ per hour.

Thus, this amount of air is itself negligible by comparison with the amount extracted from the oven 26 to be recycled, which is between 20 000 and 30 000 m$^3$ per hour.

It will therefore be understood that it is not essential also for this air laden with sterilizing agent extracted from the decontamination module 22 to be recycled.

In addition, this air has not already been filtered because it is ambient air entering the decontamination module 22 unfiltered through the openings that the enclosure 19 comprises, which means that this air does not therefore have the same degree of cleanliness as the filtered air from the oven 26.

What is more, this air has a higher concentration of sterilizing agent because it has been extracted from the sterilization chamber 21 in which the sterilizing agent is applied.

Thus, any use of this air for purposes other than those of exploiting its sterilizing properties needs to employ treatment means capable of neutralizing the sterilizing agent thereof and thus of reducing the content thereof down to a set threshold value, particularly in order to guarantee that such air is not harmful to man.

For preference, the air laden with sterilizing agent from the decontamination module 22 is therefore discharged to the atmosphere as illustrated in FIG. 6 by an arrow P in the suction pipe 55.

For preference, the discharge pipe 58 comprises means 82 of treating the sterilizing agent which are capable of neutralizing said agent so that the final sterilizing agent concentration in the air discharged to the atmosphere is less than or equal to a set threshold value.

Advantageously, the means 82 of treating the sterilizing agent are able to neutralize the agent in gaseous form using a catalysis operation.

For preference, the means 82 of treating the sterilizing agent are positioned at the junction between the suction pipe 55 and the discharge pipe 58.

When the regulating means 80 occupy some position other than the first extreme position, some of the filtered air extracted is then not recycled in the main pipe 62 and this air discharged to the atmosphere is advantageously able to reduce the concentration of the laden air from the decontamination module 22 by diluting it in this filtered air taken from the oven 26.

The operation of a recycling circuit 60 according to the second embodiment of the invention will now be described by comparison and with reference to FIG. 6.

The circulation of air from the intake of ambient air into the industrial premises until it is extracted by the extraction means 56 is identical to that already described with reference to FIG. 4 of the first embodiment and so reference will advantageously be made to it without there being any need to repeat it here in the case of the second embodiment.

According to the invention, the cooling air is extracted from the top by the extraction means 56 of the air recycling circuit 60 so that it can be recycled at least to the filling unit 48.

The filtered air thus extracted is then recycled via the main pipe 62 of the circuit 60 which conveys at least some of the air to the filling unit 48.

For preference, just part of the air is recycled here to the filling unit 48, as the flow rate of extracted air that can be recycled is higher than the air flow rate needed to establish a raised pressure in said filling unit 48.

The regulating means 80 divert some of the air corresponding to arrow A″ to the discharge pipe 58 to allow effective discharge and dilution of the air laden with sterilizing agent corresponding to arrow P.

Specifically, the quantity of filtered air extracted by the extraction means 56 for the purposes of recycling is generally greater than the quantity needed to supply the filling unit 48 when the air consumption of the former is, for example, of the order of 20 000 to 30 000 m$^3$ per hour while that of the latter is merely of the order of 10 000 m$^3$ per hour.

Thanks to the dilution obtained in the discharge pipe 58, the treatment means 82 can advantageously be eliminated while at the same time complying with the environmental standards relating to the sterilizing agent content of the air discharged into the atmosphere.

The air reaching the filling unit 48 in the direction of the arrow A′, advantageously with the assistance of the ventilation means 72, is then filtered for a second time via the filtration means 70 with which the unit 48 is equipped and is introduced into the associated interior volume 20C of the enclosure 18 in order therein constantly to maintain a raised pressure around the machines 50 and 52.

The air then escapes from the filling unit 48 via the lower part of the enclosure 18 to be returned to the industrial premises 16.

For preference, the conversion unit 38 of the installation 10 comprises, independently of the recycling circuit 60, a blowing system 57 of the type described hereinabove and of which the air consumption of the order of 8000 to 12 000 m$^3$ per hour is represented in FIG. 6 by an arrow B.

Advantageously, the blowing system 57 comprises filtration means 76 and ventilation means 78 able to suck ambient air from the industrial premises 16 to establish a raised pressure in the interior volume 20B of the unit 38 that converts the preforms 14.

The invention claimed is:

1. A plant (10) for manufacturing containers (12) from preforms (14), comprising:
   a protective enclosure (18) that isolates an interior volume (20) thereof from ambient air contained in an industrial premises (16) surrounding the protective enclosure (18);
   an oven (26) for thermally conditioning the preforms (14), the oven located within the interior volume (20) of the protective enclosure (18), the preforms (14) being thermoplastic preforms, the oven (26) comprising heating means (30);
   an air-cooling device (34) comprising i) ventilation means (32), located above the oven (26) and within the interior volume (20) of the protective enclosure (18), that draws in the ambient air contained in the industrial premises (16) surrounding the protective enclosure (18) through a wall of the protective enclosure (18), and ii) filtration means (36), located between the oven (26) and the wall of the protective enclosure (18), that filters the ambient air drawn from the industrial premises by the ventilation means (32) to form filtered air, the air-cooling device (34) introducing the filtered air exiting the filtration means (36) into the oven (26) to blow on and cool at least part of the preforms (14) in transit inside the oven (26) using said filtered air introduced by the air cooling device (34) and then to draw the air up the oven through the ventilation means for discharge out of the oven at a discharge side of the ventilation means (32);
   a conversion unit (38) for converting the preforms (14) into containers (12);
   a filling unit (48) for filling the containers (12) obtained from said preforms (14); and
   a cooling-air recycling circuit (60) comprising:
   i) extraction means (56) having an inlet side and an outlet side, the inlet side being connected to the outlet side of the ventilation means (32), the air discharged out of the oven through the ventilation means (32) being taken into the inlet side of the extraction means (56) to thereby extract, from the oven (26), the filtered air introduced into the oven (26) by the air-cooling device (34), and
   ii) at least one pipe (62, 74) having an inlet connected to the outlet side of the extraction means and an outlet connected to an air inlet of at least one of the group consisting of the conversion unit (38) and the filling unit (48) to convey at least some of said filtered air extracted from the oven (26) by the extraction means (56) into at least one of the group consisting of the conversion unit (38) and the filling unit (48), such that all or some of said air received through the wall of the protective enclosure, filtered by the filtration means (36), and then used initially for air-cooling the performs in the oven (26) is recycled at least directly into the air inlet of the at least one of the conversion unit (38) and the filling unit (48).

2. The plant (10) as claimed in claim 1, wherein the at least one pipe (62, 74) comprises a main pipe (62) with i) an upstream end connected to the outlet side of the extraction means (56) and ii) a downstream end connected to the air inlet of the filling unit (48) so that at least some of the air received through the wall of the protective enclosure, filtered by the filtration means (36), used initially for air-cooling the performs in the oven (26), and then extracted from the oven (26) by the extraction means is recycled by being introduced into said filling unit (48).

3. The plant (10) as claimed in claim 2, wherein the at least one pipe (62, 74) further comprises a branch pipe (74) with i) an upstream end connected to the main pipe (62) or to the outlet side of the extraction means (56) and ii) a downstream end connected to the air inlet of the conversion unit (38) that converts the preforms (14) into containers (12) so that at least some of the filtered air extracted from the oven (26) by the extraction means is recycled by being introduced into said conversion unit (38).

4. The plant (10) as claimed in claim 1, wherein the air inlet of one of the group consisting of the conversion unit (38) and the filling unit (48) comprise filtration means (76, 70) for filtering the air received from the at least one pipe (62, 74) of the cooling-air recycling circuit (60) that is introduced into the at least one of the group consisting of the conversion unit (38) and the filling unit (48) so as to perform double filtration on the recycled air.

5. The plant (10) as claimed in claim 1, wherein,
   the cooling-air recycling circuit (60) further comprises a discharge pipe (58) with i) an upstream end that communicates with the outlet side of the extraction means (56) and ii) a downstream end that opens into atmosphere, outside the industrial premises (16), and
   regulating means (80) arranged so as selectively to distribute the extracted air from the outlet side of the extraction means (56) into at least one of the group consisting of i) said discharge pipe (58) and ii) said at least one pipe (62, 74) of the cooling-air recycling circuit (60).

6. The plant as claimed in claim 5, further comprising a module (22) for decontaminating the preforms (14) by applying at least one sterilizing agent, wherein said decontamination module (22) comprises extraction means (53) able to suck up the air containing the sterilizing agent in the gaseous state from a sterilization chamber (21) of the module (22) so as to discharge from the module (22) said air laden with sterilizing agent via at least one suction pipe (55) the outlet of which is connected to the discharge pipe (58) that opens into the atmosphere.

7. The plant as claimed in claim 6, wherein the cooling-air recycling circuit (60) comprises treatment means able to neutralize all or some of the sterilizing agent present in the recycled air.

8. The plant as claimed in claim 7, wherein the sterilizing-agent treatment means (82) are arranged at least in the at least one pipe (62, 74) that conveys all or some of said filtered air extracted from the oven (26) to the at least one of the group consisting of the conversion unit (38) and the filling unit (48).

9. The plant as claimed in claim 7, wherein the sterilizing-agent treatment means (82) are arranged in at least one of the group consisting of said suction pipe (55) and said discharge pipe (58), in order to neutralize all or some of said sterilizing agent present in the air.

10. A method for recycling air in a plant (10) for manufacturing containers (12) from preforms (14), the plant including a protective enclosure (18) that isolates an interior volume (20) thereof from ambient air contained in an industrial premises (16), the protective enclosure (18) containing an oven (26) for thermally conditioning the preforms (14), said method comprising at least the following sequential steps:
- a) with an air-cooling device (34) comprised of i) ventilation means (32), located above the oven (26) and within the interior volume (20) of the protective enclosure (18), that draws in the ambient air contained in the industrial premises (16) through a wall of the protective enclosure (18), and ii) filtration means (36), located between the oven (26) and the wall of the protective enclosure (18), that filters the ambient air drawn from the industrial premises by the ventilation means (32) through the wall of the protective enclosure (18) to form filtered air exiting the filtration means (36) that is introduced into the oven (26) in order to cool at least part of the preforms (14) in transit inside the oven (26) using said filtered air introduced by the air cooling device (34), filtering, via the filtration means (36), the ambient air drawn in by the ventilation means (32) through the wall of the protective enclosure (18) and introducing said filtered air into the oven and onto the preforms to air-cool at least part of the preforms (14) while the preforms (14) are undergoing thermal conditioning in the oven (26);
- b) extracting the filtered air through ventilation means (32) and out from the oven (26) after said air has been used for cooling the preforms (14); and
- c) recycling at least some of said filtered air extracted from the oven (26) by piping said filtered air from an outlet of the ventilation means (32) and introducing all or some of said extracted air into an air inlet of one of the group consisting of a conversion unit (38) and a filling unit (48) of the plant (10).

11. The plant (10) as claimed in claim 1, wherein the at least one pipe (62, 74) comprises a branch pipe (74) with i) an upstream end connected to the outlet side of the extraction means (56) and ii) a downstream end connected to the air inlet of the conversion unit (38) that converts the preforms (14) into containers (12) so that at least some of the filtered air extracted from the oven (26) by the extraction means is recycled by being introduced into said conversion unit (38).

12. The plant (10) as claimed in claim 2, wherein the air inlet of one of the group consisting of the conversion unit (38) and the filling unit (48) comprise filtration means (76, 70) for filtering the air received from the at least one pipe (62, 74) of the cooling-air recycling circuit (60) that is introduced into the at least one of the group consisting of the conversion unit (38) and the filling unit (48) so as to perform double filtration on the recycled air.

13. The plant (10) as claimed in claim 3, wherein the air inlet of one of the group consisting of the conversion unit (38) and the filling unit (48) comprise filtration means (76, 70) for filtering the air received from the at least one pipe (62, 74) of the cooling-air recycling circuit (60) that is introduced into the at least one of the group consisting of the conversion unit (38) and the filling unit (48) so as to perform double filtration on the recycled air.

14. The plant (10) as claimed in claim 2, wherein,
the cooling-air recycling circuit (60) comprises a discharge pipe (58) with i) an upstream end that communicates with the outlet side of the extraction means (56) and ii) a downstream end that opens into atmosphere, outside the industrial premises (16), and
regulating means (80) arranged so as selectively to distribute the extracted air from the outlet side of the extraction means (56) into at least one of the group consisting of i) said discharge pipe (58) and ii) said at least one pipe (62, 74) of the cooling-air recycling circuit (60).

15. The plant (10) as claimed in claim 3, wherein,
the cooling-air recycling circuit (60) comprises a discharge pipe (58) with i) an upstream end that communicates with the outlet side of the extraction means (56) and ii) a downstream end that opens into atmosphere, outside the industrial premises (16), and
regulating means (80) arranged so as selectively to distribute the extracted air from the outlet side of the extraction means (56) into at least one of the group consisting of i) said discharge pipe (58) and ii) said at least one pipe (62, 74) of the cooling-air recycling circuit (60).

16. The plant (10) as claimed in claim 4, wherein,
the cooling-air recycling circuit (60) comprises a discharge pipe (58) with i) an upstream end that communicates with the outlet side of the extraction means (56) and ii) a downstream end that opens into atmosphere, outside the industrial premises (16), and
regulating means (80) arranged so as selectively to distribute the extracted air from the outlet side of the extraction means (56) into at least one of the group consisting of i) said discharge pipe (58) and ii) said at least one pipe (62, 74) of the cooling-air recycling circuit (60).

17. A plant (10) for manufacturing containers (12) from preforms (14), comprising:
a protective enclosure (18) with an interior volume (20) isolated from ambient air contained in an industrial premises (16) surrounding the protective enclosure (18);
an oven (26) for thermally conditioning the preforms (14), the oven located within the interior volume (20) of the protective enclosure (18),
the oven (26) comprising i) heating means (30) and ii) an air-cooling device (34),
the air-cooling device (34) comprising i) ventilation means (32) that draws in the ambient air contained in the industrial premises (16) surrounding the protective enclosure (18), and ii) filtration means (36) that filters the ambient air drawn from the industrial premises by the ventilation means (32) to form filtered air, the air-cooling device (34) arranged with the ventilation means being located above the over (26) and with the filtration means being located between the oven (26) and a wall of the protective enclosure (18), the air-cooling device (34) for introducing the filtered air exiting the filtration means (36) into the oven (26) to blow on and cool at least part of the preforms (14) in transit inside the oven (26), and then to draw the air up the oven through the ventilation means for discharge out of the oven at a discharge side of the ventilation means (32);
a conversion unit (38) for converting the preforms (14) into containers (12);
a filling unit (48) for filling the containers (12) obtained from said preforms (14); and
a cooling-air recycling circuit (60) comprising:
i) extraction means (56) having an inlet side and an outlet side, the inlet side being connected to the outlet side of the ventilation means (32), the air discharged out of the oven through the ventilation means (32) being taken into the inlet side of the extraction means (56) to extract, from the oven (26), the filtered air introduced into the oven (26) by the air-cooling device (34), and
ii) a first pipe (62) connected to the outlet side of the the extraction means and to an air inlet side of the conversion unit (38) and a second pipe (74) connected to the outlet side of the the extraction means and to an air inlet side of the filling unit (48) to convey said filtered air extracted from the oven (26) by the extraction means (56) into the air inlet side of the conversion unit (38) and the filling unit (48), such at least some of said air received through the wall of the protective enclosure, filtered by the filtration means (36), and then used for air-cooling the performs in the oven (26) is recycled at least directly into the air inlet of the conversion unit (38) and the filling unit (48),
wherein the preforms (14) are thermoplastic preforms.

\* \* \* \* \*